United States Patent [19]

Wong et al.

[11] Patent Number: 4,601,880

[45] Date of Patent: Jul. 22, 1986

[54] URINE CONTAINER WITH BIOCIDAL ACTIVITY

[75] Inventors: Patrick S. L. Wong, Kowloon, Hong Kong; Jimmy B. Langston, San Jose; Harold M. Leeper, Mountain View, both of Calif.

[73] Assignee: ALZA Corporation, Palo Alto, Calif.

[21] Appl. No.: 722,247

[22] Filed: Apr. 11, 1985

Related U.S. Application Data

[60] Division of Ser. No. 397,471, Jul. 12, 1982, Pat. No. 4,529,398, which is a division of Ser. No. 137,538, Apr. 4, 1980, abandoned, which is a continuation-in-part of Ser. No. 78,507, Sep. 24, 1979, Pat. No. 4,241,733, which is a division of Ser. No. 804,962, Jun. 9, 1977, Pat. No. 4,193,403.

[51] Int. Cl.$^4$ ............................................... A61L 2/00
[52] U.S. Cl. ............................................ 422/28; 422/37
[58] Field of Search ................... 523/122, 123; 422/28, 422/37

[56] References Cited

U.S. PATENT DOCUMENTS

| | | | |
|---|---|---|---|
| 785,838 | 3/1905 | Sutor | 128/283 |
| 1,080,716 | 12/1913 | Rand | 128/283 |
| 2,149,053 | 2/1939 | Hollister | 128/283 |
| 2,861,965 | 11/1958 | Roncoroni | 260/23 |
| 2,951,766 | 9/1960 | White | 523/122 |
| 3,310,235 | 3/1967 | Zbinden | 239/6 |
| 3,312,221 | 4/1967 | Overment | 128/275 |
| 3,595,607 | 1/1969 | Gores | 21/74 |
| 3,630,348 | 12/1971 | Benson | 206/63.2 R |
| 3,688,985 | 9/1972 | Engel | 239/54 |
| 3,694,146 | 8/1975 | Roy et al. | 21/119 |
| 3,719,751 | 3/1973 | Rauscher et al. | 424/27 |
| 3,754,871 | 8/1973 | Hessel et al. | 23/267 A |
| 3,772,193 | 11/1973 | Nelli et al. | 210/62 |
| 3,832,999 | 9/1974 | Crilly | 128/275 |
| 3,848,603 | 11/1974 | Throner | 128/349 R |
| 3,896,753 | 9/1972 | Shepherd | 523/122 |
| 3,898,038 | 8/1975 | Anderson | 21/58 |
| 3,942,634 | 3/1976 | Gandi et al. | 206/210 |
| 3,994,439 | 11/1976 | Van Breen et al. | 239/54 |
| 4,045,244 | 8/1977 | Lange | 134/22 R |
| 4,050,576 | 9/1977 | Williams et al. | 206/210 |
| 4,054,542 | 10/1977 | Buckman et al. | 260/2 BP |
| 4,130,433 | 12/1978 | Becker | 523/122 |
| 4,208,309 | 6/1980 | Kraemer | 523/122 |
| 4,233,263 | 11/1980 | Schaeffer | 422/28 |
| 4,263,424 | 4/1981 | Buckley | 523/122 |

FOREIGN PATENT DOCUMENTS

| | | | |
|---|---|---|---|
| 2401608 | 8/1974 | Fed. Rep. of Germany | 210/764 |
| 2088119 | 7/1972 | France . | |
| 2298952 | 1/1975 | France . | |

OTHER PUBLICATIONS

*The Condensed Chemical Dictionary* by Hawley, 8th Ed., Van Nostrand Reinhold Company, N.Y. (1975) p. 443.

*Primary Examiner*—Paul R. Michl
*Attorney, Agent, or Firm*—Paul L. Sabatine; Edward L. Mandell; Steven F. Stone

[57] ABSTRACT

A patient-care system is disclosed comprising a container housing a device that delivers an agent for controlling the presence of pathogens. Also, the device and a method are disclosed using the device for preventing pathogenic infections.

1 Claim, 7 Drawing Figures

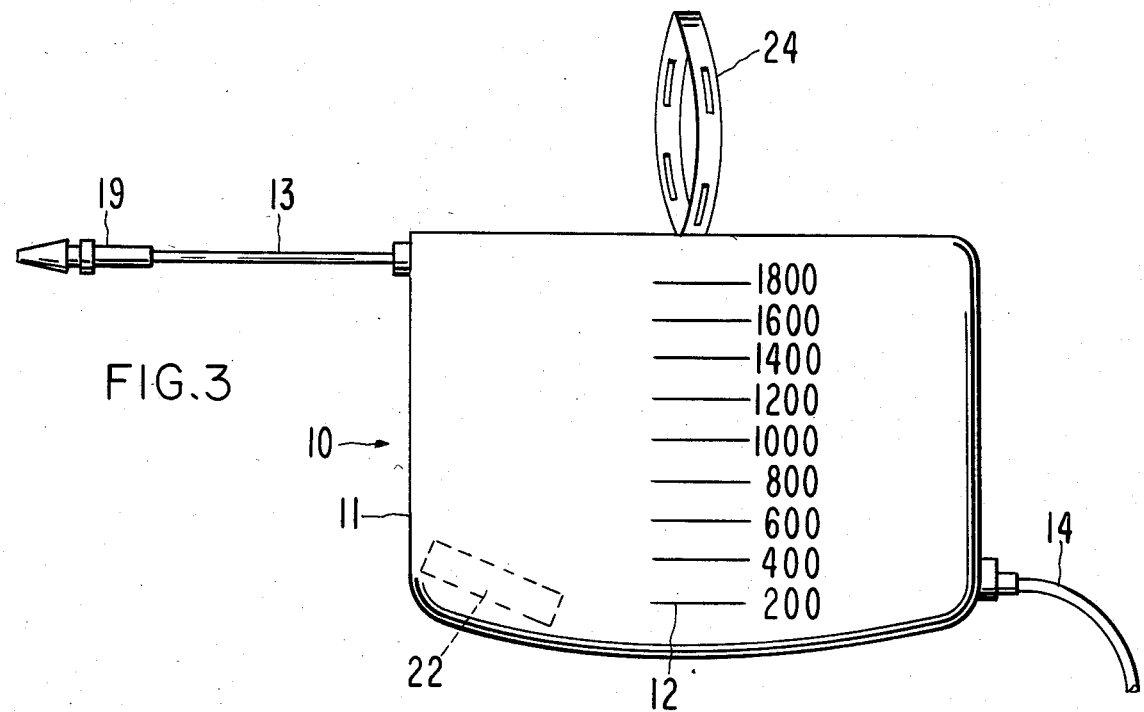
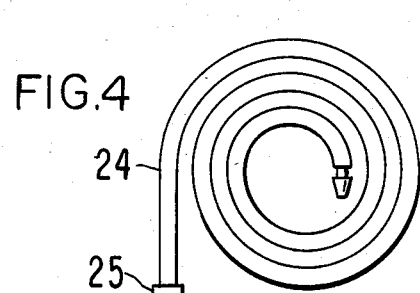
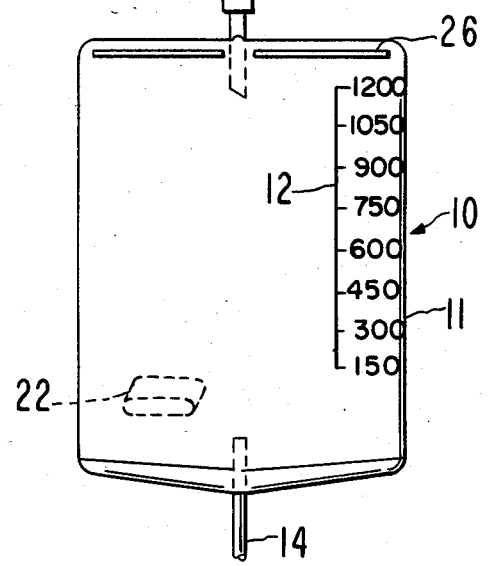
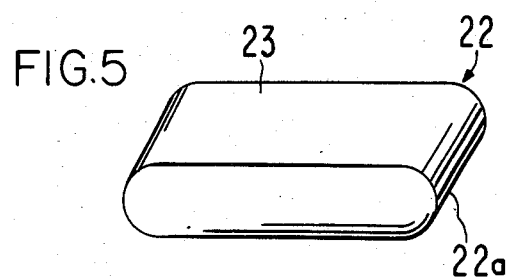
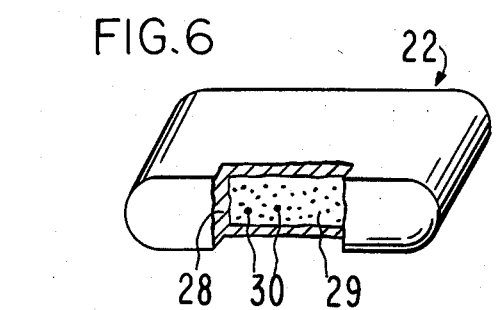
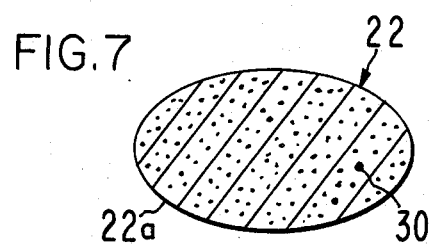

URINE CONTAINER WITH BIOCIDAL ACTIVITY

CROSS-REFERENCE TO RELATED APPLICATION

This application is a division of United States patent application Ser. No. 06/397,471 filed July 12, 1982, now U.S. Pat. No. 4,529,398, which application is a division of United States patent application Ser. No. 137,538, filed Apr. 4, 1980, now abandoned, which application is a continuation-in-part of United States patent application Ser. No. 78,507 filed on Sept. 24, 1979 now U.S. Pat. No. 4,241,733 issue Dec. 30, 1980, which application is a division of United States patent application Ser. No. 804,962 filed June 9, 1977, now U.S. Pat. No. 4,193,403. Patent applications Ser. Nos. 78,507, 804,962, 137,538 and 397,471 are incorporated herein by reference, and benefit is claimed of their filing dates. This application and Ser. Nos. 78,507, 804,962, 137,538 and 397,471 are assigned to the ALZA Corporation of Palo Alto, Calif.

FIELD OF THE INVENTION

This invention pertains to a patient-care system. More specifically, the invention related to a patient-care apparatus comprising a receptacle, a catheter having in combination with the apparatus a dispensing device that releases an agent for controlling and preventing the presence of unwanted pathogens in the entire apparatus, and more particularly in the receptacle and in the catheter. The invention also concerns a method for using the device in cooperation with the apparatus, and the device as an article of manufacture.

BACKGROUND OF THE INVENTION

It is now generally acknowledged that indwelling catheterization in medical, surgical, gynecological, urological and other patients can lead to serious infection of the urogenital tract. Despite the use of more careful aseptic techniques undertaken while the catheter is in the patient, approximately fifty percent of the patients develop an infection when a catheter is in place for twenty four hours, and approximately ninety-eight to one hundred percent of the patients develop an infection after four days of open indwelling catheter drainage. This is harmful to the patient because they are subjected to the risk of cystitis, acquired bacteriuria, acute pyelonephritis, bladder infections, and life-threatening septicemia which carries a risk of mortality, as reported in *Arch. Internal Med.*, Vol. 110, pages 703 to 711, 1962; *Antimicrob. Agents Chemother.*, pages 617 to 623; and *Lancet*, Vol. 1, pages 310 to 312, 1960.

The occurrence of the above-mentioned infections are encouraged by many circumstances. These include prolonged use of indwelling Foley catheters, the absence of sterile insertion and maintenance techniques, and having the catheter, connected to clean but not sterile drainage collection containers placed in the immediate vicinity of the patient's bed. Other sources of acquired unwanted infections include the presence of urinary infectious pathogens in the container which multiply and enter the tract through the ascending catheter, which catheter is a major pathway of infection, the use of drainage systems made without a valve designed to prevent ascending pathogen migration through the catheter, and the use of nonprofessional ward personnel for monitoring the indwelling catheter and the drainage system. These and other circumstances that predispose a patient to infection are reported in *Urinary Tract Infection and Its Management*, edited by Kaye, D., Chapter 15, *Care of the Indwelling Catheter*, pages 256 to 266, 1972, published by The C. V. Mosby Company, St. Louis, Mo.

Attempts have been made to reduce the incidence of catheter-acquired and container-propagated infections, but these have not met with general acceptance. For example, one such attempt consists in systemic chemoprophylaxis achieved by administering either chloramphenicol or penicillin and streptomycin, but this affords no significant protection against the acquisition of infection after indwelling catheterization as reported in *Arch. Internal Med.*, Vol. 110, pages 703 to 711, 1962; *Acta Chiv. Scand.*, Vol. 118, pages 45 to 52, 1959; and *Dis. Mon.*, pages 1 to 36, September 1960. Another attempt for controlling infection consists in adding formalin to the collection container. However, this method does not enjoy general use because there is a risk of siphoning formalin into the urinary tract, and more importantly, since the formalin is in the container as a liquid, it can rapidly diffuse as a gas from the container, and as such it does not provide any protection against pathogens in the drainage container, or against pathogens traveling an ascending catheter; see *British Medical Journal*, Vol. 2, pages 423 to 425, 1964. One other attempt known to the art for preventing infection consists in placing an interruption in the catheter to prevent pathogen migration from a container to the patient. The purpose of the interruption was to discourage communication of the infection to the patient, as disclosed in U.S. Pat. No. 3,750,372. This design, however, is not widely used as it lacks means for preventing pathogen multiplication in the entire collection system and because the presence of small amounts of moisture in the interruption acts as a highway for pathogens to travel to a patient. In U.S. Pat. No. 3,908,659 a one way valve is disclosed for establishing in drainage systems a barrier to pathogen migration; but this, too, is unsatisfactory because the valve retains liquid, which liquid then provides the pathogens with a path around the barrier. It will be appreciated by those versed in the art, that in view of the above presentation, a critical need exists for a patient care fluid collection system having in cooperation therewith a device for preventing and controlling the presence of unwanted pathogens in the system, and if such were made available, it would represent a valuable and useful contribution to the practicing art.

OBJECTS OF THE INVENTION

Accordingly, it is an object of the present invention to provide an improvement in patient-care apparatus which improvement overcomes the disadvantages associated with the prior art.

It is a further object of the invention to provide a patient care apparatus comprising in combination a drainage collection system and a dispensing device for preventing the multiplication of/and controlling the migration of pathogens from the system into a patient.

Still a further object of the invention is to provide a patient care apparatus consisting of a fluid collection receptacle and a catheter with a housing for holding a dispensing device that releases an agent for preventing passage of unwanted pathogens through the catheter into a mammalian host.

Still a further object of the invention is to provide a method for preventing the development of a catheter-induced infection in a patient having an indwelling catheter emptying into a fluid drainage receptacle.

Yet still a further object of the invention is to provide a method for inhibiting the migration of unwanted organisms into the lumen of a catheter emptying into a receptacle by dispensing a biocidal agent in the receptacle to produce an antiseptic environment that inhibits the migration.

Yet still a further object of the invention is to make available to the medico-surgical art a patient care urinary drainage collection system housing a dispensing device containing a polymer that is depolymerized in the presence of moisture and released from the device as an active agent that essentially discourages the communication of infection producing pathogenic organisms from the system back into the patient.

It is yet aother object of this invention to provide a urinary drainage system with a detachable housing for containing a dispensing device that releases an antipathogenic agent and which system embraces inventive simplicity, is inexpensive to make and is disposable.

Another object of the invention is to provide a container which container houses a dispensing device that releases an agent for controlling the presence of pathogens.

Yet another object of the invention is to provide a device comprising an agent that on its release from the device prevents the growth and multiplication of unwanted infectious organisms and disinfects an environment of use.

These and other objects of the present invention will become more apparent upon a consideration of the drawings, the specification and the accompanying claims.

SUMMARY OF THE INVENTION

This invention concerns a patient care apparatus comprising, in combination, a container having an inlet port, and an exit port, with the inlet port adapted for receiving a catheter. The container contains a dispensing device comprising a polymer housing a chemoprophylactic agent. The chemoprophylactic agent on its release from the device is useful for controlling and preventing the growth and multiplication of pathogens in the apparatus, and for preventing their migration into a patient. The invention also concerns the device and methods for using the device.

BRIEF DESCRIPTION OF THE DRAWINGS

In the drawings, which are not drawn to scale, but rather are set forth to illustrate various embodiments of the invention, the figures are as follows:

FIG. 3 illustrates a patient-care apparatus with a dispensing device in a drainage container;

FIG. 4 illustrates another embodiment of a patient-care system comprising a receptacle, an integral connecting tube having an interior lumen, and a chemoprophylactic delivery device in the receptacle;

FIG. 5 is a front elevational view of a biocide dispensing device provided by the invention for dispensing a biocide for producing an antiseptic environment;

FIG. 6 is a cross-sectioned view through the device of FIG. 5 illustrating a biocide dispersed in the device; and FIG. 7 is a view of the device of FIG. 5, with a section of the device cut-away, for illustrating an internal reservoir of the device.

In the specification and drawings, like parts in related figures are identified by like numbers. The terms appearing earlier in the specification and in the drawings, as well as embodiments thereof are further discussed elsewhere in the disclosure.

DETAILED DESCRIPTION OF THE DRAWINGS

Figure 1:
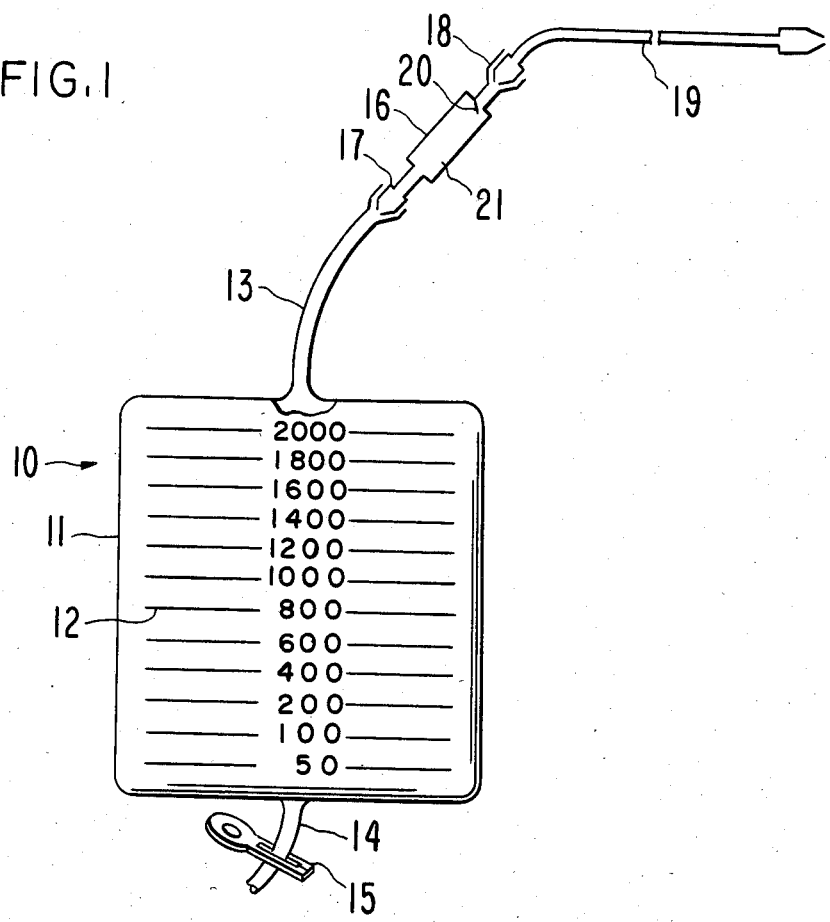
FIG. 1 is a frontal view of a patient care apparatus of the invention showing a container acting in cooperation with a detachable, exterior housing for holding a dispensing device.

Turning now to the drawings in detail, which are examples of various embodiments of the invention, and which examples are not to be construed as limiting the invention, one embodiment of a novel patient-care apparatus is indicated in FIG. 1 by numeral 10. Apparatus 10 comprises a container 11 for receiving and storing a biological fluid, not shown, and has a volumetric scale 12 thereon for indicating the volume of fluid in container 11. Apparatus 10 has an inlet port 13, or inlet tube 13, for establishing fluid passage between the interior and the exterior of container 11. A flexible outlet port 14 for draining container 11 is positioned distant from inlet port 13. Port 14 is equipped with a pinch clamp 15 for controlling the amount of fluid drained from container 11. Apparatus 10 acts in cooperation with an exterior housing 16 equipped with end 17 adapted for communicating with inlet 13 and with end 18 adapted for receiving catheter 19. In the embodiment illustrated, device 16 has a male-end at 17 for inserting into a female-end of tube 13, and device 16 has a female-end at 18 for receiving a male-end of catheter 19. In another optional embodiment, not shown, device 16 has a female-end at 17, a male-end at 18, catheter 19 has a female-end and tube 13 has a male-end. Housing 16 provides an internal space 21 for holding a dispensing device, not shown in FIG. 1. Housing 16 is equipped with a one-way valve 20 for preventing fluid passage and pathogen migration from container 11 into ascending catheter 19. In an inventive embodiment, valve 20 acts in cooperation with the dispensing device, described later, for preventing the migration of pathogens into a patient. Container 11 is made of plastic, glass and the like, and catheter 19 is made from polyethylene, nylon, and the like.

Figure 2:
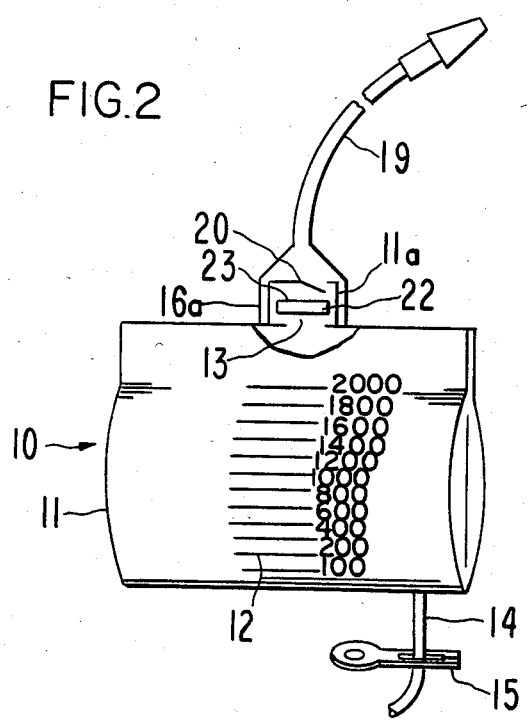
FIG. 2 is a partially frontal view of the patient care apparatus illustrating a housing for holding a dispensing device which housing is in communication with a container.

FIG. 2 illustrates a patient care apparatus 10 embracing many of the features of apparatus 10 of FIG. 1, and it also embraces additional structural features. Apparatus 10 of FIG. 2, is structurally distinct from FIG. 1, by comprising an exterior housing 16a that intimately contacts and engages container 11 by pushing it onto a projection 11a of container 11. A dispensing device 22, embracing a polymeric structure described hereafter, is housed in 16a, and device 22 has at least one-surface 23, or a multiplicity of surfaces for releasing an agent having biocidal activity. The biocide prevents migration of pathogens into ascending catheter 19. The patient care apparatus is made of plastic, glass, and like materials.

FIG. 3 illustrates an embodiment of the invention comprising a patient care apparatus 10 manufactured with the numbered features described above. In the embodiment depicted in FIG. 3, a dispensing device 22 is confined within container 11 for controlling the presence of pathogens in container 11. Device 22 controls the multiplication and precludes the survival of pathogens, or unwanted infectious organisms in container 11 by continually dispensing at a controlled rate biocidally effective amounts of a biocide into container 11. Device 22 by dispensing a biocide for the aseptic management of container 11, concomitantly inhibits and prevents the migration of infectious organisms into catheter 19. This invention embodiment substantially prevents the development of catheter induced infections in a patient that are introduced through an indwelling catheter; which indwelling catheter passes through the urethra into the bladder, and drains the bladder through the catheter tubing connected to fluid drainage receptacle 11. In FIG. 3, apparatus 10 is made with a handle 24 for hanging container 11 from a stand placed in the vicinity of a patient's bed.

FIG. 4 illustrates a urinary drainage apparatus 10, similar to the above Figures, and in this Figure it also comprises additional structural features. In the present embodiment, apparatus 10 is manufactured with an integral connecting tube 24, connected to container 11, through a releasable connector 25, and it has a suspension rod 26 for hanging the container. Apparatus 10 comprises in combination, container 11 housing device 22 that dispenses a biocide for producing an antiseptic environment. The term biocide, as used herein, means an agent that destroys, inhibits, prevents and the like, the propagation, growth, multiplication and the like of unwanted organisms. The term organisms includes microorganisms, bacteria, undulating bacteria, spirochetes, spores, spore-forming organisms, gram-negative organisms, gram-positive organisms, yeasts, fungi, molds, viruses, aerobic, anerobic, mycobacteria, and the like.

FIG. 5 illustrates a device 22 used for dispensing a biocidal agent. Device 22 consists essentially of a body 22a sized, shaped and adapted for placement in the environment of use. Device 22 is used for disinfecting an article of manufacture, in a presently preferred embodiment, a fluid container. Device 22 has at least one surface 23, or device 22 has a multiplicity of surfaces for dispensing a biocide from device 22. Body 22a can embrace any preselected geometric shape, such as square, round, rectangle, triangle, crescent, and the like. Device 22 can be manufactured as a sheet, film, strip, envelope, cylindrical rod, solid matrix, sponge, prism of various cross-sections, such as cruciform, hexagonal, and the like. Device 22 also can be manufactured as a container, as seen in FIG. 6, with an internal compartment 29, housing biocide 30, represented by dots. FIG. 7 is a cross-section through FIG. 5. As seen in FIG. 7, device 22 comprises a body 22a having biocide 30 dispersed therein, which biocide is released over time for destroying or inhibiting the growth of organisms in a preselected environment of use.

While the environment of use in a presently preferred use is a fluid drainage system as discussed in detail herein, it is to be understood the environment of use also includes hospital rooms, laboratories, animal quarters, bathrooms, vehicles, swimming pools, water, fumigate stored citrus fruits, railroad cars, irrigation canals, animal dips and the like. The phrase article of manufacture includes germ-free boxes, garment bags, mattresses, pillows, covers, garbage cans, surgical robes, surgeon's gloves, medical instruments, and like articles in need of disinfecting, or protection against unwanted organisms.

Additional Details of the Invention

Dispensing device 22 used for the purpose of the invention consists of a body 22a formed of a polymeric material that maintains its physical and chemical integrity during use. The polymer permits the release of biocide 30 from device 22, and it can be permeable to the passage of fluid. The polymeric material can be a homopolymer, copolymer, a microporous polymer, a cross-linked polymer and the like. Representative polymers suitable for forming the body include acrylic polymers and copolymers of methylmethacrylate; homopolymers and copolymers of vinyl chloride including vinyl chloride-vinyl acetate copolymer; chlorinated vinylchloride; polyethylene; polypropylene; ethylene-propylene copolymer; chlorinated polyethylene; ethylenevinyl acetate copolymer; styrene-butadiene copolymer; acrylonitrile-styrene-butadiene-terpolymer; polyvinylidene chloride; vinyl-chloride-acrylonitrile copolymer; vinylidene chloride-acrylate ester copolymer; polybutylene terphthalate; vinyl chloride-acrylate ester copolymer; cross-linked polyvinyl acetals such as cross-linked polyvinyl formal; cross-linked polyvinyl butyral; polyethers; sparingly cross-linked polyesters; polyurethanes; chlorosulfonated polyolefins; polyolefins; polyisoprene; polybutadiene; polysilicone; and the like. The polymers are disclosed in the *Handbook of Common Polymers*, by Scott et al, 1971, published by CRC Press, Cleveland, Ohio; in *Modern Plastics Encyclopedia*, 1979, published by McGraw-Hill Inc., New York, N.Y.; and in *Handbook of Plastics and Elastomers*, by Harper, 1976, published by McGraw-Hill Inc., San Francisco, Calif.

The biocides used for the purpose of the invention, embrace in a presently preferred embodiment the polymer paraformaldehyde. The paraformaldehyde polymer used as a biocide is a member selected from the group consisting of the cyclic tripolymer of the general formula $(CH_2O)_n$ wherein n is 3, and the linear polymer of the general formula $HO(CH_2O)_mH$ wherein m is 3 to 125. These polymers are white crystalline solids, and in the presence of moisture they undergo depolymerization to yield the water soluble biocide and disinfectant formaldehyde; see the *Encyclopedia of Chemical Technology*, by Kirk Othmer, Vol. 10, pages 81, 1966, published by John Wiley & Sons, Inc., New York. In operation, device 22 formed of a first polymer houses the different depolymerizable polymer paraformaldehyde that is moisture-activated by fluid entering the first polymer from the surrounding causing (1) the depolymerizable polymer to depolymerize to formaldehyde which formaldehyde vapors or as a solution containing formaldehyde migrate to the exterior of the device, or (2) the depolymerizable polymer migrates to the exterior of the device, and in the presence of moisture it is converted to vaporous formaldehyde or to a solution containing the biocide formaldehyde. In either operation, formaldehyde acts as a biocide, or disinfectant to control the presence of microorganisms. The amount of cyclic or linear paraformaldehyde housed in the device can vary depending on the need, and it will usually be about 0.001% to 60% by weight based on the total weight of the device. Generally, in the presence of moisture, or in the presence of moisture and an acid catalyst, the cyclic and linear polymers are converted up to 99% formaldehyde, which is released over a prolonged period of time. For devices made of a polymer having low permeability to moisture, including water and biological fluids, the time can be a year or longer.

The biocides used for the mode and the manner of the invention as housed in device 22, also include a member selected from the group consisting essentially of a phenol, quaternary ammonium, surfactant, chlorine-containing, quinoline, quinaldinium, lactone, antibiotics, dye, thiosemicarbazone, quinone, sulfa, carbamates, urea, salicylamide, carbanilide, amide, guanide, amidine, chelate and imidazoline biocides.

Exemplary biocidal dyes include acridine, acriflavine, aminacrine hydrochloride, proflavin hemisulfate, triphenylmethane, magenta, crystal violet, scarlet red, pararosaniline, and rosaniline. Exemplary chlorine releasing biocides include sodium hypochlorite, oxychlorosene, chloramine, dichlorodimethylhydantoin, halazone, dichloramine, chlorasine, succinchlorimide, trichloroisocyanuric acid, dichloroisocyanurate, trichloromelamine, dichloroglycoluril, halogenated dialkyl-hydantoin, and halane.

Exemplary biocidal quinaldinium and quinoline biocides are dequalinium, laurolinium, hydroxyquinoline, lioquinol, chlorquinaldol and halquinol. Exemplary quaternary ammonium biocides include pyridinium biocides, benzalkonium chloride, cetrimide, benzethonium chloride, cetylpyridinium chloride, chlorphenoctium amsonate, dequalinium acetate, dequalinium chloride, domiphen bromide, laurolinium acetate, methylbenzethonium chloride, myristyl-gamma-picolinium chloride, ortaphonium chloride, and triclobisonium chloride. Exemplary furans include greseofulvin, nitrofurfural, nitrofurazone, nitrofurantoin, furazolidone, and furaltadone.

Exemplary phenol biocides include a member selected from the group consisting essentially of chlorinated phenol, cresol phenol, thymol, chlorocresol, chloroxylenol, hexachlorophane, bisphenols, amylmetacresol, bithionol, chlorothymol, dichloroxylenol, chlorophene, p-chlorophenol, p-phenylphenol, trinitrophenol, dichlorobisphenol, and bromochlorobisphenol. Exemplary antibiotics include penicillins, aminoglycosides, benzylpenicillin, ampicillin, tetracyclines, cephalosporins, chloramphenicol, vancomycin, fucidin, rifampicin, cephaloridine, erythromycin actinomycin, neomycin, polymyxin, colistin, gentamicin, carbenicillin and streptomycin. Exemplary lactones include propiolactone. Exemplary urea biocides include noxytiolin, polynoxylen and triclocarban.

Examples of other biocides useful for the purpose of the invention are chlorhexidine gluconate, chlorhexidine, chlorhexidine acetate, chlorhexidine hydrochloride, dibromopropamidine, halogenated diphenylalkanes, dibromsalan, metabromsalan, tribromsalan, carbanilide, salicylanilide, tetrachlorosalicylanilide, trichlorocarbanilide, propamidine isethionate, pentamidine, picloxydine, mendalamine, methenamine salts, the acid addition and quarternary, methenamine mandelate, polyoxymethylene esters such as polyoxymethylene diester, polyoxymethylene diacitate and the like, and mixtures thereof.

The amount of biocides in a device generally will be about 0.1% to 80% by weight, with a more preferred amount of 10% to 50% by weight. The devices can be manufactured for releasing anti-infective amounts of biocide over prolonged periods from several hours to 30 days or longer, with a more preferred period of 2 to 16 days. The devices of the invention are manufactured for releasing from 10 ng to 500 mg per hour, or higher, of biocide, and in one presently preferred embodiment from 25 $\mu$g to 150 $\mu$g per ml of fluid drained into a container. The biocides are disclosed in *Disinfection, Sterilization and Preservation,* by Block, 1977, published by Lea & Febiger, Philadelphia, Pa.; in *Inhibition and Destruction of Microbial Cells,* by Hugo, 1971, published by Academic Press, New York; and in *Martindale, The Extra Pharmacopoeia,* Edited by Blacow, published by The London Pharmaceutical Press, London.

DETAILED DESCRIPTION OF EXAMPLES

The following examples will serve to further illustrate the present invention, but the invention is not intended to be limited thereto.

EXAMPLE 1

A dispensing device of tubular shape was made as follows: first 45 grams of powdered, white solid polymeric paraformaldehyde were blended for 10 to 15 minutes at 35° to 45° C., on a two-roll mill, with 55 grams of powdered, transparent ethylenevinyl acetate copolymer, having a vinyl acetate content of 28% by weight, to produce a film consisting essentially of a homogenous dispersion of depolymerizable paraformaldehyde in the copolymer. Next, the film was ground in a rotary grinder to produce particles sized 1/16 to ⅛ inches, average size, and the particles then transferred to the hopper of an extruder. Finally, the particles were extruded through a tubing die at 60° to 70° C. to yield the dispensing device. The device had an outside diameter of 5.2 mm, an inside diameter of 2.2 mg, and a length of 5 cm. The dispensing device exhibited a steady-state delivery of an effective amount of free formaldehyde when the device was moisture activated, at the rate of 220 $\mu$g/hr-cm of device, which is effective for preventing micro-organism growth. The device is non-erodible and keeps its integrity during residence in the environment of use. The manufacture of the device is described in our copending patent application Ser. No. 804,961 filed on June 9, 1977, and now U.S. Pat. No. 4,144,309 issued on Mar. 13, 1979. The patent is assigned to the ALZA Corporation.

EXAMPLE 2

A dispensing device of rectangular shape is made as follows: first, 40 grams of powdered paraformaldehyde is blended for 10 to 15 minutes at 35° to 40° C., on a two-roll rubber mill with 50 grams of ethylene-vinyl acetate copolymer having a vinyl content of 28%, and 10 grams of powdered citric acid, to produce a film consisting essentially of a homogenous dispersion of paraformaldehyde and citric acid in the copolymer. Next, the film is ground in a rotary grinder to produce particles sized 1/16 to ⅛ inches, average size, and the particles then transferred to the hopper of an extruder. Finally, the particles are extruded through a dye at 60° to 70° C. to yield the dispensing device useful for preventing bacteria growth.

EXAMPLE 3

The procedure of Example 2 is repeated, except that the acid is replaced with an acid selected from the group consisting essentially of malic, fumaric, tartaric, Lewis acid, phthalic, itaconic, maleic, adipic, succinic, mesaconic, amygladic, sulfamic, boric acid, and mixtures thereof, which organic and inorganic acids produce an acidic state within the device as an aid for controlling the rate of generation of formaldehyde from paraformaldehyde. The Lewis acid includes ferric chloride, aluminum chloride, stannic chloride, boron trichloride and mixtures thereof.

EXAMPLE 4

A device for dispensing methenamine useful as an anti-infective is manufactured by following the procedure of Example 1. In this device, the ethylene-vinyl acetate polymer has a vinyl acetate content of 18%, and the device contains 50 grams of methenamine.

EXAMPLE 5

A device for dispensing methenamine mandelate useful as an anti-infective is made as follows: first 40 grams of white crystals of methenamine mandelate are ground to a powdered state and fed to a two roller mill for bonding with ethylene-vinyl acetate copolymer having a vinyl acetate content of 18%, to produce a film consisting of methenamine mandelate in the copolymer. The film is removed from the mill, cut into sections, fed to an extruder, and extruded as a device, shaped, sized and structured for placement in the environment of use.

EXAMPLE 6

The procedure of Example 5 is repeated with the methenamine mendelate replaced with a member selected from the group consisting essentially of methenamine camphorate, methenamine iodoform, methenamine salicylate, methenamine sulfosalicylate, methenamine tetraiodide and methenamine anhydromethylene citrate, and the copolymer is replaced with a member selected from the group consisting of ethylene-vinyl propionate copolymer, poly(ethylene), and microporous polyurethane. The device maintains its integrity in the presence of fluids, solids, gels and pathogens.

EXAMPLE 7

The procedure of Example 5 is followed, with the methenamine acid addition salt selected from sulfamate, bitartrate, oxalate, hydrochloride, and quarternary salts.

EXAMPLE 8

27.5 grams of micronized particles of methenamine mandelate having a particle size of 40 microns, and 12.5 grams of micronized particles of tartaric acid having a particle size of 40 microns are thoroughly mixed for about 5 to 10 minutes in an internal Banbury mixer to yield a predevice forming composition. Next, the composition is fed over a 5 to 10 minute period to a two-roll rubber mill previously charged with ethylene-vinyl acetate-acrylic acid terpolymer consisting of 28% vinyl acetate, 1% acrylic acid and the remainder ethylene for 5 to 10 minutes for surrounding the composition with the terpolymer. Then, the milled product is passed through a four-roll calender to form a film. Finally, the film is die-cut into devices 8 cm×2 cm×1 cm. The presence of the organic acid in the polymer produces the functional equivalent pH range of 5 to 6.5, leading to the production of mandelic acid and the hydrolysis of methenamine to formaldehyde.

EXAMPLE 9

The above procedures are repeated with the anti-infective biocide chlorhexidine, methenamine iodobenzylate, methenamine camphorate, methenamine allyl iodide, methenamine hippurate, methenamine hydriodide, or methenamine tetraiodide.

The biocide and disinfectant are dispensed by the device to kill, cleanse, prevent and/or retard the presence or propagation of harmful or unwanted micro-organisms as defined supra. The micro-organisms include the fungi *Aspergillus niger, Aspergillus flavus, Rhizopus nigricans, Cladosporium herbarium, Epidermophyton floccosum, Trichophyton mentagrophytes, Histoplasma capsulatum,* and the like. The term micro-organisms also includes antibacterial activity against *Pseudomonas aeruginosa, Escherichia coli, Proteus vulgaris, Staphyloccus aureus Streptococcus faecalis, Klebsiella, Enterobacter aerogenes, Proteus mirabilis,* other gram-negative bacteria and other gram-positive bacteria, mycobactin and the like. The term also embraces yeast such as *Saccharomyces derevisiae, Canndida Albicans,* and the like. Additionally, spores of micro-organisms, viruses and the like, are within the intent of the invention.

The release rate of the biocide formaldehyde from a device made according to Example 1 is demonstrated in water solutions containing 0 to 5% sodium chloride corresponding to osmotic pressures of 0 to 43 atmospheres. The rate of formaldehyyde release, expressed as the average steady-state release rate at listed sodium chloride concentration, is given in Table 1.

TABLE 1

| NaCl Concentration In Release Solutions (wt %) | Osmotic Pressure In Release Solutions (atm) | Steady-State Release Rate μg/hr-cm |
|---|---|---|
| 0 | 0 | 232 |
| 0.9 (isotonic) | 7.9 | 220 |
| 2.4 | 20.3 | 226 |
| 5.0 | 43 | 196 |

In Table 1, wt% is the abbreviation for weight percent, atm for atmospheres, the steady-state release rate was measured for 30 to 240 hours and is expressed as μg/hr per cm of length of dispensing device. The data indicate five 5 cm dispensing devices of the above-described dimensions and parameters will deliver to a patient care apparatus 5 mg/hr for up to 10 days in a high osmolarity environment up to 43 atmospheres the needed formaldehyde. The data further indicate the release rate of formaldehyde is independent from the osmolarity of the release solution containing an osmagent such as the osmotic agent sodium chloride.

It will be understood by those versed in the medico-surgical and patient-care arts, that in the light of the present specification, drawings and the accompanying claims, this invention makes available to the art both a novel and useful combination patient care and a dispensing device endowed with beneficial properties. And, while the invention can be used for collecting all kinds of biological fluids and other fluids, it will be further understood by those versed in the art that many embodiments of this invention can be made without departing from the scope of the invention. Accordingly, it is to be understood the invention is not to be construed as limited, but it embraces all equivalents inherent herein.

We claim:

1. A method of aseptic management in and urine collecting reservoir, which method consists of substantially inhibiting the multiplication and precluding the survival of unwanted organisms in the reservoir, the method comprising: (1) admitting into the reservoir a polymeric body formed of a material that substantially maintains its physical and chemical integrity in the presence of fluid admitted into the reservoir, and contains a biocide effective member selected from the group consisting of methenamine mandelate, methenamine camphorate, methenamine iodoform, methenamine salicylate, methenamine sulfosalicylate, methenamine tetraiodide, methenamine anhydromethylene citrate, methenamine sulfamate, and polyoxymethylene ester for inhibiting the multiplication and precluding the survival of the organisms, and contains an acid for producing an acidic pH within the polymer; and (2) releasing the biocide from the polymeric body at a controlled rate in a biocidal effective amount into the reservoir over a prolonged period of time for obtaining the desired results.

* * * * *